United States Patent
Zou et al.

(10) Patent No.: US 9,687,638 B2
(45) Date of Patent: Jun. 27, 2017

(54) SWALLOWABLE MEDICATION CAPSULE

(75) Inventors: Hans Zou, Chappaqua, NY (US); Jeff Shimizu, Cortlandt Manor, NY (US)

(73) Assignee: Medimetrics Personalized Drug Delivery, Charlotte, NC (US)

(*) Notice: Subject to any disclaimer, the term of this patent is extended or adjusted under 35 U.S.C. 154(b) by 0 days.

(21) Appl. No.: 14/006,901

(22) PCT Filed: Mar. 23, 2012

(86) PCT No.: PCT/US2012/030332
§ 371 (c)(1),
(2), (4) Date: Jan. 17, 2014

(87) PCT Pub. No.: WO2012/129497
PCT Pub. Date: Sep. 27, 2012

(65) Prior Publication Data
US 2014/0135698 A1  May 15, 2014

Related U.S. Application Data

(60) Provisional application No. 61/467,057, filed on Mar. 24, 2011.

(51) Int. Cl.
*A61M 31/00* (2006.01)
*A61K 9/48* (2006.01)

(52) U.S. Cl.
CPC .......... *A61M 31/00* (2013.01); *A61M 31/002* (2013.01); *A61K 9/4808* (2013.01)

(58) Field of Classification Search
CPC ..... A61B 5/073; A61B 5/4839; A61B 5/0031; A61M 31/002; A61M 31/00; A61K 9/4808
(Continued)

(56) References Cited

U.S. PATENT DOCUMENTS 5,167,626 A * 12/1992 Casper et al. ............. 604/891.1
5,279,607 A * 1/1994 Schentag et al. .......... 604/890.1
(Continued)

FOREIGN PATENT DOCUMENTS

CN  101516257  8/2009
JP  2010504135  2/2010
(Continued)

OTHER PUBLICATIONS

Extended European Search Report mailed Jan. 31, 2014 for European patent application No. 12759922.3, 6 pages.
(Continued)

*Primary Examiner* — Bradley Osinski
(74) *Attorney, Agent, or Firm* — Lee & Hayes, PLLC

(57) ABSTRACT

The invention relates to a swallowable medication capsule capable 200 of dispensing fluid medicine stored in a medication compartment 211 through a valveless exit hole 207. A vent hole 206 enables ventilation of an actuator cavity 212 which houses an actuator used for displacing a surface 205 which separates the medication cavity 211 and the actuator cavity 212. By locating the vent and exit holes close to each other so that contact with contracting parts of the gastrointestinal tract and the exterior surface 221 is not able to prohibit a pressure passageway between the vent and exit holes, creation of a pressure difference of pressures in the medication and actuator cavity is prohibited.

19 Claims, 5 Drawing Sheets

(58) Field of Classification Search
USPC .................................................. 604/19, 302
See application file for complete search history.

(56) References Cited

U.S. PATENT DOCUMENTS

| | | | |
|---|---|---|---|
| 5,395,366 A * | 3/1995 | D'Andrea et al. .......... 604/890.1 |
| 6,270,787 B1 * | 8/2001 | Ayer .................... A61K 9/0004 424/422 |
| 6,440,069 B1 * | 8/2002 | Raymond et al. ............ 600/300 |
| 6,453,199 B1 * | 9/2002 | Kobozev ........................ 607/40 |
| 7,382,263 B2 * | 6/2008 | Danowski et al. ........ 340/572.1 |
| 7,797,033 B2 * | 9/2010 | D'Andrea et al. ............ 600/424 |
| 7,978,064 B2 * | 7/2011 | Zdeblick et al. ........ 340/539.12 |
| 2002/0193669 A1 * | 12/2002 | Glukhovsky ................. 600/302 |
| 2005/0147559 A1 | 7/2005 | von Alten |
| 2008/0269664 A1 | 10/2008 | Trovato et al. |
| 2008/0306360 A1 * | 12/2008 | Robertson et al. ........... 600/302 |
| 2009/0009332 A1 * | 1/2009 | Nunez et al. .............. 340/572.1 |
| 2010/0049120 A1 | 2/2010 | Dijksman et al. |
| 2010/0063486 A1 * | 3/2010 | Dijksman ........... A61M 31/002 604/890.1 |
| 2010/0145316 A1 | 6/2010 | Mintchev et al. |
| 2010/0298668 A1 * | 11/2010 | Hafezi et al. ................. 600/302 |
| 2010/0331827 A1 | 12/2010 | Shimizu |
| 2011/0017612 A1 | 1/2011 | Dijksman et al. |
| 2012/0010590 A1 | 1/2012 | Imran |

FOREIGN PATENT DOCUMENTS

| | | |
|---|---|---|
| WO | WO2008038199 | 4/2008 |
| WO | WO2010116304 | 10/2010 |
| WO | WO2012129497 A3 | 9/2012 |

OTHER PUBLICATIONS

PCT Search Report for PCT Application No. PCT/US2012/030332, mailed Sep. 25, 2012 (3 pages).

Translated Chinese Office Action mailed Jan. 27, 2015 for Chinese patent application No. 201280014766.4, a counterpart foreign application of U.S. Appl. No. 14/006,901, 13 pages.

European Office Action mailed Dec. 15, 2015 for European Patent Application No. 12759922.3, a counterpart foreign application of U.S. Appl. No. 14/006,901, 4 pages.

Translated Chinese Office Action mailed Dec. 30, 2015 for Chinese Patent Application No. 201280014766.4, a counterpart foreign application of U.S. Appl. No. 14/006,901, 17 pages.

Translated Japanese Office Action mailed Jan. 12, 2016 for Japanese Patent Application No. 2014-501274, a counterpart foreign application of U.S. Appl. No. 14/006,901, 5 pages.

Translated Chinese Office Action mailed Jul. 29, 2016 for Chinese patent application No. 201280014766.4, a counterpart foreign application of U.S. Appl. No. 14/006,901, 13 pages.

* cited by examiner

SWALLOWABLE MEDICATION CAPSULE

PRIORITY APPLICATION

This Application is a 35 U.S.C. 371 National Stage Entry of and claims priority to PCT Application Serial No. PCT/US12/30332, entitled "Swallowable Medication Capsule," filed on Mar. 23, 2012, which claims priority to U.S. Provisional Application Ser. No. 61/467,057, entitled "Swallowable Medication Capsule", filed on Mar. 24, 2011, both of which are hereby incorporated by reference in their entirety.

FIELD OF THE INVENTION

The invention relates to a swallowable medication capsule, and in particular to avoiding unintended dispense of fluid medication.

BACKGROUND OF THE INVENTION

Swallowable electronic medication capsules are used for dispensing fluid medication to a patient. Preferably, the medication should be dispensed when the swallowable capsule is at a particular location in the gastrointestinal tract, e.g. in the small intestine. However, the medication may be dispensed inadvertently due to local pressure differences that are generated by peristaltic movements. This incidence arises particularly for medicine containers comprising a flexible closure member and without valves.

Accordingly, it is problem that electronic medication capsules may dispense fluid medication inadvertently due to actions on the capsule caused by peristaltic movements of the gastrointestinal tract.

US 2008269664 discloses a treatment system provided for traversing the alimentary tract. The system includes an ingestible capsule, which includes a gas pressurizing module providing a gas and at least one balloon in fluid communication with the gas pressurization module. The capsule further includes an exhaust channel in fluid communication with a respective balloon of the at least one balloon, and a depressurizing closure member for selectively controlling flow of gas between the balloon and the ambient surroundings of the capsule. The system further includes control circuitry for controlling the depressurizing closure member.

The inventor of the present invention has appreciated that an improved medication capsule is of benefit, and has in consequence devised the present invention.

SUMMARY OF THE INVENTION

It would be advantageous to achieve improvements of medication capsules, in particular, improvements which alleviates the above mentioned problem or, or other problems, of the prior art.

The better address one or more of these concerns, in a first aspect of the invention a swallowable medication capsule having an elongate shape is presented, where the capsule comprises:
  a wall forming an exterior surface of the capsule,
  a medication compartment for containing a displacement actuator,
  a displaceable surface arranged to be driven by the displacement actuator, where the medication compartment is partly defined by the displaceable surface,
  a dispense channel providing a passageway between the medication compartment and an exit hole formed at the exterior surface for dispensing the fluid medication to the surroundings.
  a vent channel providing a passageway between the actuator compartment and a vent hole formed at the exterior surface,
  where a separation between the exit hole and the vent hole along an elongate axial direction of the elongate shape is less than the length of the medication compartment along the elongate axial direction.

Since the exit and vent holes are located relatively close, and at least closer than the length of the medication compartment, the holes will most likely experience the same environment pressure even if they are both blocked by the gastrointestinal wall at the same time. Therefore, the risk that different pressures are generated in the actuator and medication compartments is minimized.

The medication compartment may be defined at least partly by a part a first interior surface of the capsule, possibly an interior surface of the wall of the capsule. Also the actuator compartment may be partly defined by a part of a second interior surface of the capsule. Thus, the first and second interior surfaces may be different interior surfaces of the capsule or the same interior surface of the capsule.

The medication may be in the form of a fluid, a liquid, a gas, a gel or solid particles such as a powder.

In an embodiment the surface normal to the exterior surface at the location of the exit hole is substantially parallel with the surface normal to the exterior surface at the location of the vent hole. This means that if the vent and exit holes are located on a curved surface such as an ellipsoidal surface, then the holes may be located so close that the surface normal of exterior capsule surface at the location of the holes may be substantially parallel.

In an embodiment the surface normal to the exterior surface at the location of the exit hole and the surface normal to the exterior surface at the location of the vent hole are substantially perpendicular to the elongate axial direction. This means that if the vent and exit holes are located on a curved surface such as an ellipsoidal surface, then the holes may be located so close that the surface normal of exterior capsule surface at the location of the holes may be substantially perpendicular to the axial direction of the elongate capsule. If the capsule is cylindrical in shape, then the surface normal of the vent and exit holes are perpendicular to the axial direction of the cylindrical shape.

In an embodiment, the exterior surface of the capsule is formed by a cylindrical shell part having an exterior cylindrical surface, where the displaceable surface is arranged in the interior of the cylindrical part so that the displaceable surface divides the interior into adjacent sections forming the medication compartment and the actuator compartment, and where the exit hole and the vent hole are located on the same exterior cylindrical surface.

In an embodiment a part of the dispense channel and/or the vent channel extends within the wall of the capsule between two different locations on the exterior wall surface. Advantageously, the inlet to the dispense channel or the vent channel may be located at a different point of the elongate shape than the associated exit hole or vent hole to facilitate unconstrained location of the inlet holes and the vent and exit holes, e.g. for improved expelling of the medication.

In an embodiment the dispense channel which extends within the wall of the capsule has different channel directions so that at least one part of the channel provides a fluid passageway in a direction against the gravity, irrespective of the orientation of the swallowable medication capsule.

In an embodiment the dispense channel and/or the vent channel is formed as a groove in an outer shell of the capsule in combination with an inner shall providing a closure of the groove and where the inner shall has a hole providing a fluid passageway between the medication compartment and the groove.

In an embodiment the displaceable surface forms a fluid tight separation between the medication compartment and the actuator compartment. Thus, the displaceable surface may be membrane which forms a wall of the medication compartment which separates the medication compartment from the actuator compartment.

In an embodiment the capsule is constituted by a first part and a second part which are connectable, where the medication compartment is a self-confined entity comprised by the second part, and the actuator compartment is a self-confined entity comprised by the first part.

A second aspect of the invention relates to a method for providing a swallowable medication capsule having an elongate shape, where the capsule has a wall forming an exterior surface of the capsule, the method comprises
  providing a first part of the capsule where the first part comprises,
    an actuator compartment for containing a displacement actuator,
    a vent channel providing a passageway between the actuator compartment and a vent hole formed at the exterior surface, and
  providing a second part of the capsule where the second part comprises,
    a medication compartment for containing a medication.
    a displaceable surface arranged to be driven by the displacement actuator, where the medication compartment is partly defined by the displaceable surface,
    a dispense channel providing a passageway between the medication compartment and an exit hole formed at the exterior surface for dispensing the fluid medication to the surroundings,
  where the first and second parts are connectable to form the elongate shaped capsule, and where the separation between the exit hole and the vent hole along an elongate direction of the elongate shape, when the first and second parts are connected, is less than the length of the medication compartment along the elongate direction.

Advantageously, the medication compartment may be comprised by a separate part which is connectable another part which comprises the actuator compartment. Thus, the part comprising the actuator compartment may be reused, whereas the part comprising the medication compartment may be disposable.

In general the various aspects of the invention may be combined and coupled in any way possible within the scope of the invention. These and other aspects, features and/or advantages of the invention will be apparent from and elucidated with reference to the embodiments described hereinafter.

In summary the invention relates to a swallowable medication capsule capable 200 of dispensing fluid medicine stored in a medication compartment 211 through a valveless exit hole 207. A vent hole 206 enables ventilation of an actuator cavity 212 which houses an actuator used for displacing a surface 205 which separates the medication cavity 211 and the actuator cavity 212. By locating the vent and exit holes close to each other so that contact with contracting parts of the gastrointestinal tract and the exterior surface 221 is not able to prohibit a pressure passageway between the vent and exit holes, creation of a pressure difference of pressures in the medication and actuator compartment is prohibited.

BRIEF DESCRIPTION OF THE DRAWINGS

Embodiments of the invention will be described, by way of example only, with reference to the drawings, in which.

DESCRIPTION OF EMBODIMENTS

Figure 1:
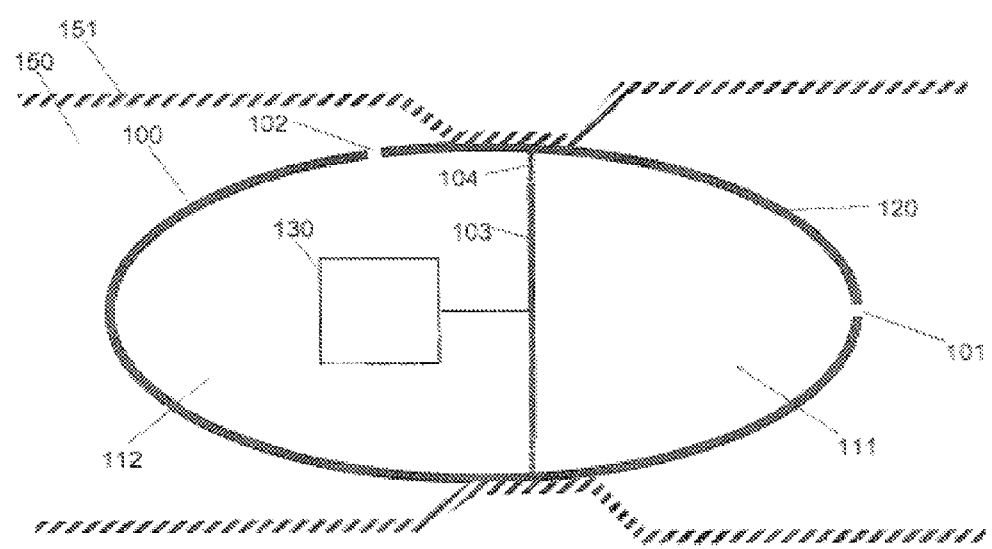
FIG. 1 shows a medication capsule 100 for illustration of a contraction of the gastrointestinal tract 150 which prohibits free fluid communication between the vent hole 102 and the dispensing exit hole 101.

FIG. 1 shows a cross sectional view of swallowable medication capsule 100 designed to be swallowed by a patient and to dispense fluid medicine at a target location, e.g. when the capsule passes the small intestine. The capsule 100 includes an outer wall 120, a medication compartment 111, an actuator compartment 112 containing an actuator 130, and a displaceable element 103 connected to the inner surface of the wall 120 by a flexible member 104. The actuator 130 is capable of displacing the displaceable element 103 so as to reduce the volume of the medication compartment. The surface of the displaceable element 103 and the flexible member 104 together with the interior surface of the wall 120 defines the cavity of the medication compartment 111. Accordingly, the displaceable member 103 is in fluid communication with the medication compartment 111 as well as the actuator compartment 112. Fluid medication contained in the medication compartment 111 can be expelled to the surrounding environment of the capsule via a dispense channel 101 formed in the wall 120 by action of the displacement actuator 130.

When the displaceable element 103 is pushed toward the medication compartment 111, there will be a void space left behind in the actuator compartment. Therefore a vent channel 102 in the wall 120 is provided to equalize pressure differences between the environment and the actuator compartment. Thus, the displaceable element 103 can displace without need to overcome additional resistance due to under pressure from its previous advancement.

Since part of the medication compartment is made of the flexible member 104 and the displaceable element 103, medication could be partially expelled if there is unbalanced pressure applied to the flexible member 104 and the displaceable element 103. This may happen when the capsule experiences contractions of the gastrointestinal walls. If pressure communication through the vent channel 102 between the actuator compartment and medication compartment is not blocked, the flexible member 104 and element 103 will not experience unbalanced pressure.

However, when the capsule 100 passes through the gastrointestinal tract 150, peistaltic movements of the wall 151 of the gastrointestinal tract causes contractions of the wall which may block pressure communication between the vent channel 102 and the dispense channel 101. Thereby, a higher pressure in the actuator compartment may arise which presses against the flexible member 104, thereby causing an undesired expelling of medication via the dispense channel 101.

Figure 2:
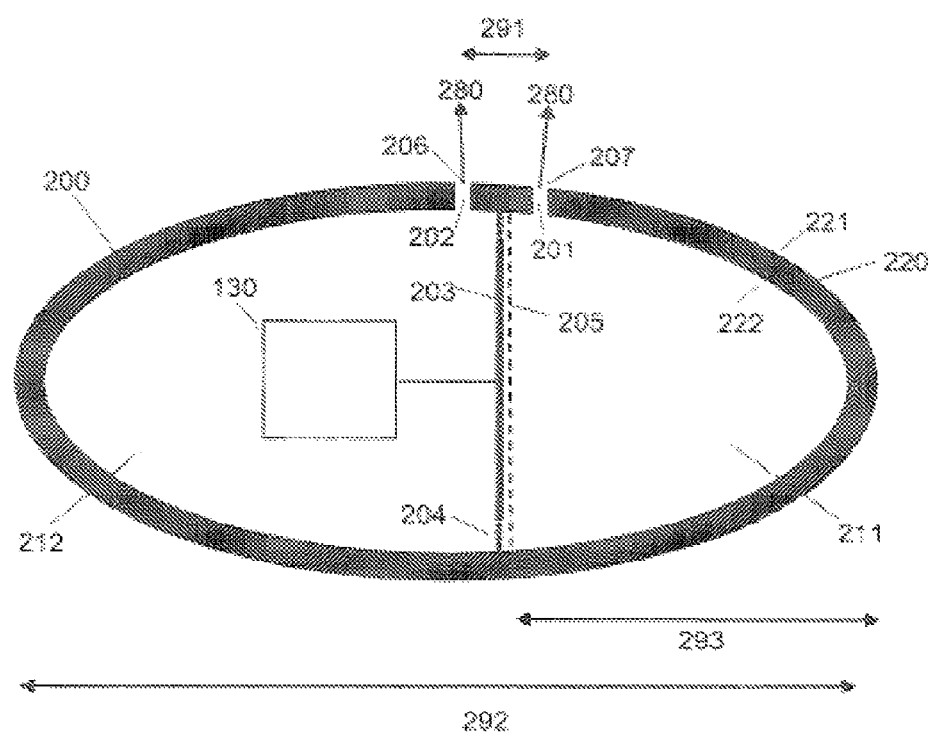
FIG. 2 shows a medication capsule 200 according to an embodiment of the invention where the vent hole 202 and the dispensing exit hole 201 are arranged close to each other.

FIG. 2 shows a cross sectional view of a medication capsule according to an embodiment of the invention to avoid blockage of pressure communication between the actuator compartment and the medication compartment. The capsule 200 comprises an outer wall 220 having an exterior surface 221 and an interior surface 222, where the interior surface defines a hollow interior of the capsule.

the capsule may have an ellipsoidal shape as shown in FIG. 1, a spherical shape, cylindrical shape or other shapes being suitable for a swallowable capsule.

The capsule 200 further comprises a medication compartment 211 which is bounded partly by the interior surface 222, and an actuator compartment 212 which is also bounded partly by another part of the interior surface 222. The actuator compartment 212 is intended to house a displacement actuator 130. The displacement actuator 130 may be a linear motor driven piston.

The capsule 200 further comprises a displaceable surface 205 arranged to be driven by the displacement actuator 130. The displaceable surface may be made up by surfaces of a displaceable element 203 which makes a fluid tight fit to the interior surface 222 of the wall 220. As an example, the fluid tight fit may be embodied by a flexible member 204, such as a bellows, connected to displaceable element 203 and the surface 222 of the wall 220. In this example, the displaceable element 203 is displaceably connected to the displacement actuator 130 so that the displaceable element 203 can be pushed into the medication compartment 211. The displaceable element 203, possibly in combination with the flexible member 204, forms a fluid tight displaceable surface 205 between the medication compartment and the actuator compartment. Accordingly, the displaceable surface 205 forms a wall of the medication compartment 222.

Thus, the displaceable surface 205 may be embodied in different ways. Additional examples comprise an elastic foil and a flexible wall with a rolling-sock seal connected to the interior surface 221 of the wall 220. It is understood that the displaceable surface 205 may be constituted by a physical entity such as a flexible wall or membrane, or the displaceable surface may merely be the surface of several components such as the surface 205 of the displaceable element 203 in combination with the flexible member 204. Thus the displaceable surface 205 forms a fluid tight wall of the medication compartment 211.

The actuator 130 is capable of displacing the displaceable surface 205, e.g. by displacing the displacing element 203 which may be stiff or elastic, so as to reduce the volume of the medication compartment. The displaceable surface 205 together with the interior surface of the wall 120 defines the cavity of the medication compartment 111. Accordingly, the medication compartment 211 is defined at least in part by the facing side of the displaceable surface 205 facing the medication compartment and the interior surface 222.

Fluid medication contained in the medication compartment 211 can be expelled, by action of the displacement actuator 130, to the surrounding environment through via a dispense channel 201 providing a passageway between the medication compartment 211 and an exit hole 207 formed at the exterior surface 221 of the wall 220.

A vent channel 202 is provided to enable equalization of pressures in the medication compartment and the actuator compartment. The vent channel 202 provides a passageway between the actuator compartment 212 and a vent hole 206 formed in the exterior surface 221 of the wall 220 for enabling an air flow between the actuator compartment and the surroundings.

The vent channel 202, the dispense channel 201, the displaceable element 203 and the flexible member 204 have the same function as already described in connection with FIG. 1.

In the embodiment shown in FIG. 2, the distance 291 between the vent hole 206 and the exit hole 207 has been reduced so that when the wall 151 of gastrointestinal tract 150 contacts the exterior surface 221, then it is more likely that both holes are experience the same environmental pressure or are in fluid communication. Thereby, the risk that peristaltic movements of the of the gastrointestinal tract causes different pressures in the actuator and medication compartments it minimized.

The swallowable medication capsule has an elongate shape such as an ellipsoid shape. The elongate shape of the capsule defines an elongate direction defined by a line connecting the extremities, i.e. points on the exterior surface 221 located farthest from each other. The length 292 is defined by the distance between the mentioned extremities. Accordingly, the medication capsule may have any enlongately shaped exterior shape; that is, a shape that generally has a length which is larger that the width of the shape. The elongate direction may further define a rotation symmetric axis of the elongate body. An axis may be defined being perpendicular to the elongate direction, which perpendicular axis has a length between intersection points with the exterior shape which is smaller than the length 292 between the mentioned extremities. The perpendicular axis may further define a second rotation symmetric axis of the elongate body. Examples of the elongately shaped body comprises an ellipsoid, a cylinder having rounded ends such as ellipsoid or spherically shaped ends, egg-shaped bodies which are only rotation symmetric about the elongate direction, and other arbitrarily shaped bodies.

The length 292 of the capsule may be in the range from 5 to 35 mm. Generally, the advantage of locating the vent and exit holes close for prohibiting different pressures in the actuator and medication compartment may be obtained when the axial distance (distance along the elongated direction of the capsule body) 291 between the vent hole 206 and the exit hole 207 are in the range is minimized, e.g. from 0.1 to 10 mm, preferably in the range between 0.1 to 3 mm measured as the shortest axial distance between edges of the holes. Since capsules 200 may vary in length depending on types of capsules, the effect of avoiding pressure differences may be obtained when the separation 291 between the exit hole and the vent hole along the elongate direction of the elongate capsule is less than one quarter of the length 292 along the elongate direction of the capsule. Alternatively, the effect of avoiding pressure differences may be obtained when the separation 291 between the exit hole and the vent hole along an elongate direction of the elongate shape of the capsule is less than the axial length 293 of the medication compartment measured from the axial point on the displaceable surface along the elongate axial direction to the distal axial point on the exterior surface.

As shown in FIG. 2, when the vent hole 206 and the exit hole 207 are located close to prohibit pressure differences, the surface normals 280 of the vent and exit holes are substantially parallel, i.e. the angle between the surface normals is less than 10 degrees. The surface normal 280 of the holes is defined as the surface normal to the exterior 221 of the capsule at the location (e.g. center location) of the exit hole 206 or at the location of the vent hole 207.

Equivalently, the location of the vent hole 206 and the exit hole 207 may be defined by the criteria that the surface normal 280 to the exterior of the capsule at the location of the exit hole and the surface normal 280 to the exterior of the capsule at the location of the vent hole are substantially perpendicular to the elongate direction, since the vent and exit holes may be located on a surface of the capsule which is substantially parallel with the elongate direction. For example, the exterior of an elongate capsule may be cylindrical in shape and the vent and exit holes may be located on the same cylindrical surface, i.e. locations characterized in that the surface normal 180 at the location of the holes are normal to the elongate direction or the symmetry axis of the cylinder shaped exterior surface.

The dispense channel 201 and/or the vent channel 202 may be formed as a through hole in the wall 220 perpendicular to the exterior surface 221. However, the dispense or vent channels need not be straight channels where the entrance hole to the channel and the exit hole or the vent hole are placed adjacent to each other.

Figure 3A:
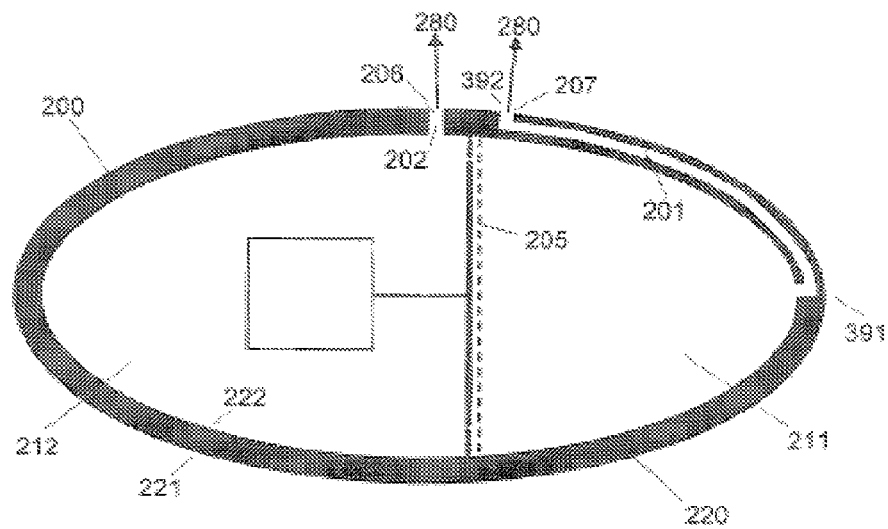
FIGS. 3A and 3B illustrate that the inlet to the vent or dispensing channel may be located remote from the respective vent or exit holes.
Figure 3B:
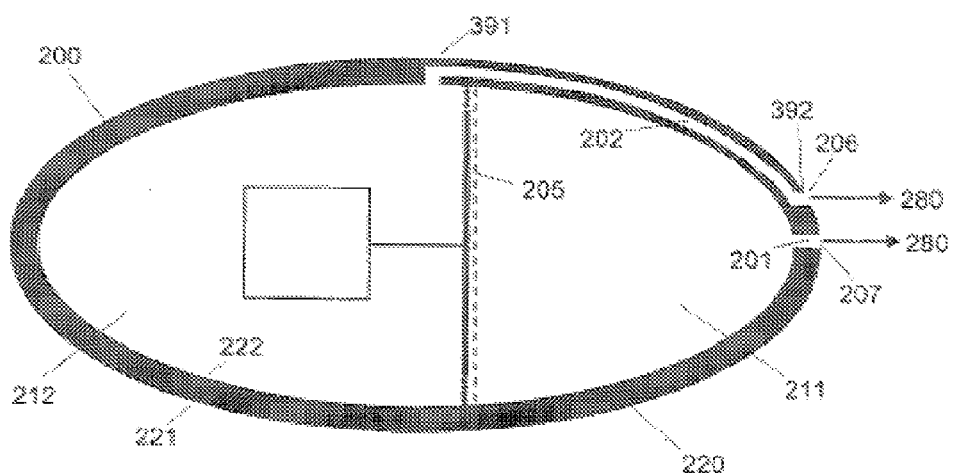

FIG. 3A shows an embodiment of the capsule 200 where a part of the dispense channel 201 extends within the wall 220 of the capsule parallel with the exterior surface 221 of the wall between two different locations at the exterior wall surface, e.g. first 391 and second 392 locations. FIG. 3B shows an embodiment of the capsule 200 where a part of the vent channel 202 extends within the wall 220 of the capsule between two different locations at the exterior wall surface, i.e. first 391 and second 392 locations. Accordingly, either one or both of the dispense channel 201 or the vent channel 202 may extend for some distance within the wall 220.

Channels 201, 202 which extends along the wall 220 enables the entrance hole of the channels to be located at the interior surface 222 at a location different from the location of the vent hole 206 or the exit hole 207. Thereby, the vent and exit holes may placed at arbitrary locations on the exterior surface 221, e.g. at the apex of the capsule, or the entrance hole of the dispense channel may be placed at the apex of the interior surface 222 to facilitate the best expulsion of the fluid medicine whereas the exit hole is located close to the vent hole at a different exterior surface part.

Figure 4:
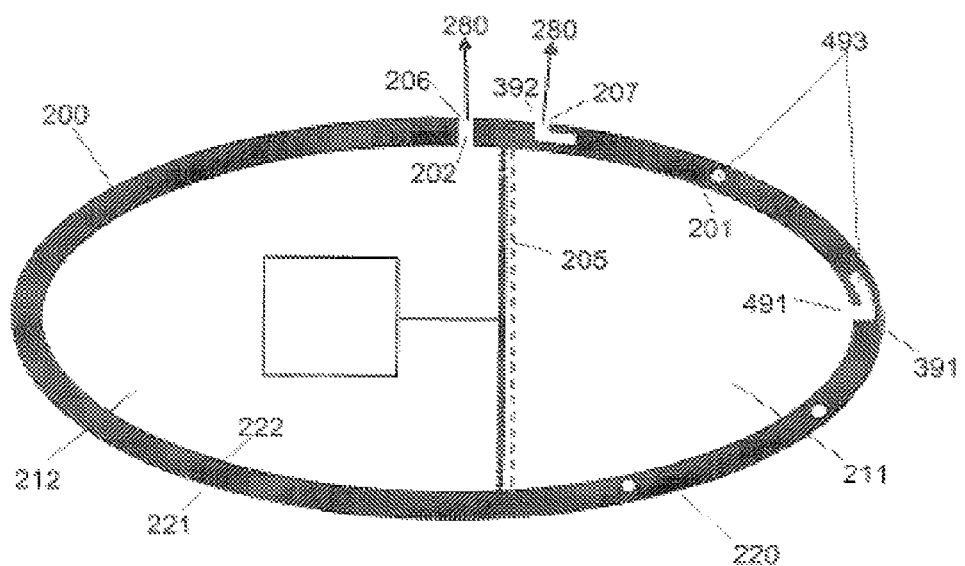
FIG. 4 shows a dispense channel formed as a serpentine to avoid dispense due to influence by the gravity force.

FIG. 4 sows a cross sectional view of the capsule where the dispense channel extends along a spiral or serpentine path within the wall from the apex 491 to the exit hole 207 located approximately halfway between apexes of the elongate shell. The spiral shape is visible as the cross sectional view 493 of the channel. Thus, in an embodiment according to the invention, the dispense channel extends within the wall in a way so that the channel has different directions so that at least one part of the channel provides a fluid passageway in a direction against the gravity (e.g. pointing into the paper in FIG. 4), irrespective of the orientation of the swallowable medication capsule. By shaping the channel so that one part of the passageway always points against the direction of gravity then the fluid medication, at least in a part of the dispense channel, will be affected by gravity in a direction that will force the fluid medication back towards the medication compartment so that unintended dispense is achieved.

Figure 5:
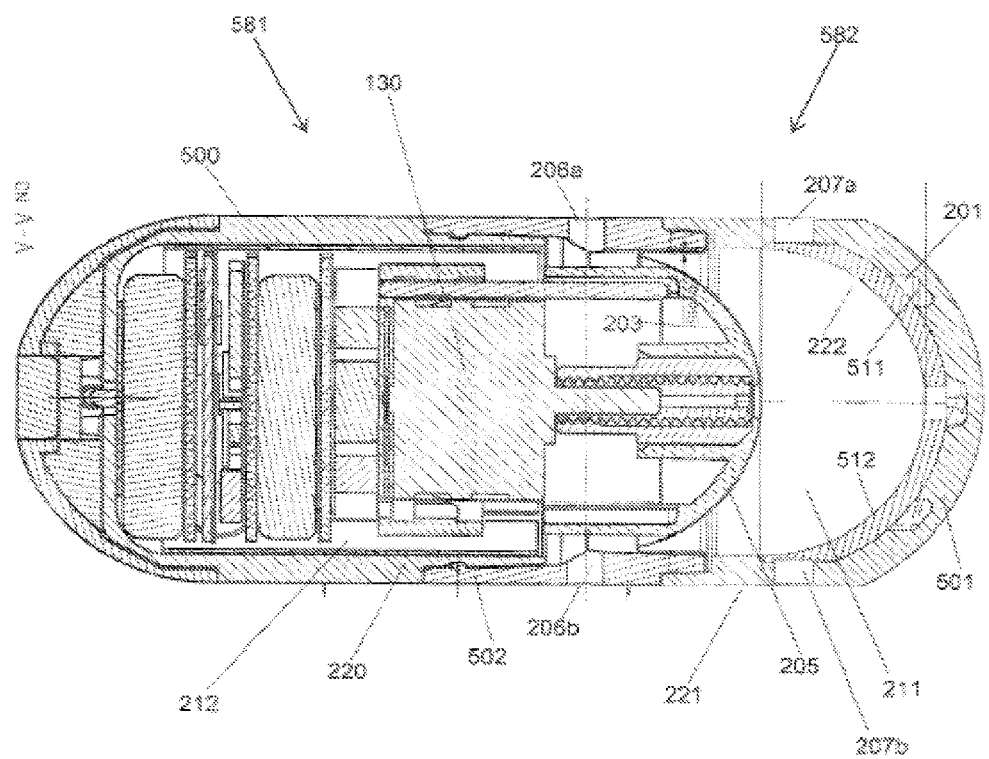
FIG. 5 shows a detailed example of a medication capsule.

FIG. 5 shows an example of a medication capsule 500 in detail. The elongate exterior surface 221 of the wall 220 of the medication capsule 500 is cylindrical in shape. The wall 220 is made up of different shell portions, such as shell portions 501 and 502. The displaceable surface 205 is embodied by an elastic membrane which divides the interior volume of the cylindrical surface 221 of the capsule 500 to form the medication compartment 211 and the actuator compartment 212. The elastic membrane is arranged to be deformed and pushed into the medication compartment by a displaceable element 203 which is displaceably contacted by a piston actuator 130.

In general the capsule 200, 500 may comprise one or more vent holes 206 as well as exit holes 207 and associated vent and dispense channels, for example first and second vent holes 206a, 206b and first and second exit holes 207a, 207b as shown in FIG. 5.

In FIG. 5 the exit hole 207a and the vent hole 206a are located on the same cylindrical surface 221 implying that the vent and exit holes can be located sufficiently close to minimize the risk of different pressures in the medication and actuator compartments.

In FIG. 5 the dispense channel 201 propagates within the wall 200 to form a serpentine channel so that a part of the passageway of the channel always points against the direction of gravity so as to minimize the risk of unintended leakages of medication due to gravity influences.

The dispense channel 201 is formed as a groove 511 in the outer shell 501 of the capsule in combination with an inner shell 512 which closes the groove 511 to form the channel. The inner shell 512 is provided with a through hole 513 to provide a passageway from the medication compartment 211 to the dispense channel 201. Thus, vent channels 202 and dispense channels 201 may be formed by a grove in an outer or inner shell part in combination with a matching inner or outer shall part.

The capsule may be assembled from first and second parts 581, 582 which are connectable to form the elongate shaped capsule.

The first part 581 comprises the actuator compartment 212, the displacement actuator 130, the vent channel 202 and the associated vent hole 206.

The second part 582 comprises the medication compartment 211, the dispense channel 201 and the associated exit hole 207, and the displaceable surface 205 when the displaceable surface is in the form of a foil or membrane which forms a fluid tight circumferential connection with the interior surface 222 of the wall 220 of the second part. Accordingly, the membrane is capable of being displaced by the displacement actuator 530 when the first and second parts are assembled.

Accordingly, the medication compartment comprised by the second part 582 may be a self-confined entity connectable with the first part 581 comprising the actuator compartment. In this way the medication compartment and actuator compartment may be comprised by separate first and second parts 581, 582 which are attached together before use.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A swallowable medication capsule having an elongate shape, the capsule comprising,
a wall forming an exterior surface of the capsule,
a medication compartment configured to contain a medication,
an actuator compartment;
a displacement actuator disposed in the actuator compartment,
a displaceable surface separating the medication compartment from the actuator compartment and arranged to be driven by the displacement actuator, where the displaceable surface is fixed to and forms a fluid-tight seal with an interior surface of the wall and the medication compartment is defined by the displaceable surface and the interior surface of the wall,
a dispense channel providing a passageway between the medication compartment and an exit hole formed at the exterior surface for dispensing the fluid medication to the surroundings, and
a vent channel providing a passageway between the actuator compartment and a vent hole formed at the exterior surface,
where a separation between the exit hole and the vent hole along an elongate axial direction of the elongate shape is less than the length of the medication compartment along the elongate axial direction,
where a part of the dispense channel and/or the vent channel extends within the wall of the capsule between two different locations on the exterior wall surface, and
where the vent channel inlet is disposed along the elongate axial direction on a side of the displaceable surface, opposite the medication compartment.

2. A capsule according to claim 1, where a surface normal to the exterior surface at the location of the exit hole is substantially parallel with the surface normal to the exterior surface at the location of the vent hole.

3. A capsule according to claim 1, where a surface normal to the exterior surface at the location of the exit hole and the surface normal to the exterior surface at the location of the vent hole are substantially perpendicular to an elongate axial direction.

4. A capsule according to claim 1, where the exterior surface of the capsule is formed by a cylindrical shell part having an exterior cylindrical surface, where the displaceable surface is arranged in an interior of the cylindrical part so that the displaceable surface divides the interior into adjacent sections forming the medication compartment and the actuator compartment, and where the exit hole and the vent hole are located on the same exterior cylindrical surface.

5. A capsule according to claim 1, where the dispense channel extending within the wall of the capsule has different channel directions so that at least one part of the dispense channel provides a fluid passageway in a direction against the gravity, irrespective of the orientation of the swallowable medication capsule.

6. A capsule according to claim 1, where the dispense channel and/or the vent channel is formed as a groove in an outer shell of the capsule in combination with an inner shell providing a closure of the groove and where the inner shell has a hole providing a fluid passageway between the medication compartment and the groove.

7. A capsule according to claim 1, where the displaceable surface forms a fluid tight separation between the medication compartment and the actuator compartment.

8. A capsule according to claim 1, where the capsule is constituted by a first part and a second part which are connectable, and where the medication compartment is a self-confined entity comprised by the second part, and the actuator compartment is a self-confined entity comprised by the first part.

9. A swallowable medication capsule having an elongate shape, the capsule comprising,
a wall forming an exterior surface of the capsule,
a medication compartment for containing a medication,
an actuator compartment for containing a displacement actuator,
a displaceable surface arranged to be driven by the displacement actuator, where the medication compartment is partly defined by the displaceable surface,
a dispense channel providing a passageway between a dispense channel inlet opening to the medication compartment and an exit hole formed at the exterior surface for dispensing the fluid medication to the surroundings, and
a vent channel providing a passageway between a vent channel inlet opening to the actuator compartment and a vent hole formed at the exterior surface,
wherein at least one of a part of the dispense channel or a part of the vent channel extends within the wall such that a spacing between the dispense channel inlet and the vent channel inlet is different from a spacing between the exit hole and the vent.

10. A capsule according to claim 9, where a surface normal to the exterior surface at the location of the exit hole is substantially parallel with the surface normal to the exterior surface at the location of the vent hole.

11. A capsule according to claim 9, where a surface normal to the exterior surface at the location of the exit hole and the surface normal to the exterior surface at the location of the vent hole are substantially perpendicular to an elongate axial direction.

12. A capsule according to claim 9, where the exterior surface of the capsule is formed by a cylindrical shell part having an exterior cylindrical surface, where the displaceable surface is arranged in an interior of the cylindrical part so that the displaceable surface divides the interior into adjacent sections forming the medication compartment and the actuator compartment, and where the exit hole and the vent hole are located on the same exterior cylindrical surface.

13. A capsule according to claim 9, where the dispense channel extends within the wall of the capsule in different channel directions so that at least one part of the dispense channel provides a fluid passageway in a direction against gravity, irrespective of the orientation of the swallowable medication capsule.

14. A capsule according to claim 9, where the dispense channel and/or the vent channel is formed as a groove in an outer shell of the capsule in combination with an inner shell providing a closure of the groove and where the inner shell has a hole providing a fluid passageway between the medication compartment and the groove.

15. A capsule according to claim 9, where the displaceable surface forms a fluid tight separation between the medication compartment and the actuator compartment.

16. A capsule according to claim 9, where the capsule is constituted by a first part and a second part which are connectable, and where the medication compartment is a self-confined entity comprised by the second part, and the actuator compartment is a self-confined entity comprised by the first part.

17. A capsule comprising:
a wall forming an exterior of the capsule,
a medication compartment configured to contain a medication;
an actuator compartment separated from the medication compartment by a displaceable surface;
a displacement actuator disposed in the actuator compartment to selectively displace the displaceable surface to alter the volume of the medication compartment;
a dispense channel providing a passageway between an opening to the interior of the medication compartment and an exit hole formed at an outer surface of the wall; and
a vent channel providing a passageway between an opening in the actuator compartment and a vent hole formed at the exterior surface,
wherein a separation between the exit hole and the vent hole along an axial direction of the capsule is less than the length of the medication compartment along the elongate axial direction, and
wherein at least one of (a) a part of the dispense channel extends within the wall such that the opening to the interior of the medication compartment and the exit hole are not co-axial and (b) a part of the vent channel extends within the wall such that the opening in the actuator compartment and the vent hole are not co-axial.

18. A capsule according to claim 17, wherein the dispense channel extending within the wall of the capsule has different channel directions so that at least one part of the channel provides a fluid passageway in a direction against the gravity, irrespective of the orientation of the swallowable medication capsule.

19. A capsule according to claim 17, wherein the dispense channel and/or the vent channel is formed as a groove in an outer shell of the capsule in combination with an inner shell providing a closure of the groove and where the inner shell has a hole providing a fluid passageway between the medication compartment and the groove.

* * * * *